(12) United States Patent
Howell et al.

(10) Patent No.: US 9,086,357 B2
(45) Date of Patent: Jul. 21, 2015

(54) CONDUCTIVITY SENSOR

(75) Inventors: Colin Howell, St. Neots (GB); David Albone, St. Neots (GB); David Edward Coe, St. Neots (GB)

(73) Assignee: ABB Limited, Gloucestershrie (GB)

( * ) Notice: Subject to any disclaimer, the term of this patent is extended or adjusted under 35 U.S.C. 154(b) by 1423 days.

(21) Appl. No.: 12/518,097

(22) PCT Filed: Dec. 5, 2007

(86) PCT No.: PCT/GB2007/004657
§ 371 (c)(1),
(2), (4) Date: Jul. 23, 2010

(87) PCT Pub. No.: WO2008/068484
PCT Pub. Date: Jun. 12, 2008

(65) Prior Publication Data
US 2010/0292944 A1    Nov. 18, 2010

(30) Foreign Application Priority Data

Dec. 6, 2006  (GB) .................................. 0624426.3

(51) Int. Cl.
| | | |
|---|---|---|
| G01R 27/08 | (2006.01) | |
| G01N 27/07 | (2006.01) | |
| G01N 27/08 | (2006.01) | |

(52) U.S. Cl.
CPC ................ *G01N 27/07* (2013.01); *G01N 27/08* (2013.01)

(58) Field of Classification Search
CPC ................. G01N 27/403; G01N 27/07–27/08
USPC ......... 324/439, 442, 444, 446, 447, 449, 450, 324/600; 73/335.05, 861.12, 861.15, 304 R; 249/83, 85, 91, 96; 425/112, 117, 123, 425/125, 127
See application file for complete search history.

(56) References Cited

U.S. PATENT DOCUMENTS 3,714,555 A    1/1973   Greer
3,746,891 A *  7/1973   Rowe ............................ 327/129
(Continued)

FOREIGN PATENT DOCUMENTS

DE    42 33 110       4/1994
EP    0 542 140 A2    5/1993
(Continued)

OTHER PUBLICATIONS

PCT International Search Report for PCT Counterpart Application No. PCT/GB2007/004657 containing Communication relating to the Results of the Partial International Search Report, 3 pgs., (Mar. 6, 2008).
(Continued)

*Primary Examiner* — Thomas F Valone
(74) *Attorney, Agent, or Firm* — Blakely, Sokoloff, Taylor & Zafman LLP

(57) ABSTRACT

A conductivity sensor is described in which electrodes are held in a desired position within a housing of the sensor by a number of slots accurately positioned within the housing. In one embodiment the slots are integrally formed within the housing. Once the electrodes have been inserted into the slots a thermoset resin is poured into the housing and cured. A through bore is then drilled through the housing, the electrodes and the cured resin to form a flow conduit through the sensor. A dual frequency excitation technique is also described that allows a measurement to be obtained of a polarisation resistance of the electrodes. In one embodiment this measurement is stored and used to correct subsequent conductivity measurements.

20 Claims, 6 Drawing Sheets

(56) References Cited

U.S. PATENT DOCUMENTS

| | | | | |
|---|---|---|---|---|
| 3,890,420 | A | * | 6/1975 | Neward .......... 264/261 |
| 3,919,738 | A | | 11/1975 | Scmall |
| 3,936,729 | A | | 2/1976 | Winslow, Jr. |
| 3,980,944 | A | | 9/1976 | Gallant et al. |
| 3,993,945 | A | | 11/1976 | Warmoth et al. |
| 4,287,150 | A | * | 9/1981 | Gendron .......... 264/538 |
| 4,824,406 | A | * | 4/1989 | Vause .......... 439/864 |
| 4,831,324 | A | | 5/1989 | Asakura et al. |
| 5,315,847 | A | | 5/1994 | Takeda et al. |
| 6,377,052 | B1 | | 4/2002 | McGinnis et al. |
| 2003/0076662 | A1 | * | 4/2003 | Miehling .......... 361/760 |

FOREIGN PATENT DOCUMENTS

| | | |
|---|---|---|
| EP | 1 098 197 | 5/2001 |
| FR | 2 766 271 | 1/1999 |
| GB | 869226 | 5/1961 |
| GB | 1 460 892 | 1/1977 |
| GB | 1 517 697 | 7/1978 |
| GB | 2 057 141 A | 3/1981 |
| JP | 03210466 | 9/1991 |
| JP | 2001188054 A | 7/2001 |
| WO | WO 89/09396 | 10/1989 |
| WO | WO 94/03802 A1 | 2/1994 |

OTHER PUBLICATIONS

Patents Act 1977: Search Report under Section 17 for United Kingdom Counterpart Application No. GB0624426.3, 1 pg., (Jul. 10, 2007).

Extended European Search Report for EP Counterpart Patent Application No. 13159261.0-1554, 2 pgs. (May 28, 2013).

First Office Action for corresponding Chinese Patent Application No. 201310456926.7, 7 pp. (only English translation), (Feb. 28, 2015).

PCT Written Opinion of the International Search Authority for PCT/GB2007/004657, 7 pgs. (Jun. 6, 2009).

PCT International Preliminary Report on Patentability for PCT Application No. PCT/GB2007/004657, 8 pgs. (Jun. 10, 2009).

* cited by examiner

CONDUCTIVITY SENSOR

CROSS-REFERENCE TO RELATED APPLICATIONS

This patent application is a U.S. National Phase application under 35 U.S.C. §371 of International Application No. PCT/GB2007/004657, filed on Dec. 5, 2007, entitled CONDUCTIVITY SENSOR, which claims priority to Great Britain patent application number 0624426.3, filed Dec. 6, 2006.

FIELD

The present invention relates to conductivity sensors, to parts therefor and to their method of manufacture.

BACKGROUND

Conductivity meters are well known and established products and have use in a number of applications, such as dialysis machines, power systems and water treatment systems. The applicant has been selling conductivity sensors for approximately 40 years. Typically, conductivity sensors include a conductivity cell having at least two electrodes that are accurately spaced apart along a flow tube. In order to accurately space the electrodes, they are typically made by machining elongate carbon rods. In particular, the carbon rod is machined to leave the electrodes of the required shape (usually disk shaped) and which are separated by the required spacing and held in place by a central part of the graphite rod that is not machined away. Connections are then made to the electrodes using circlips and wire that is soldered to the circlips. This electrode structure is then placed in a mould and a thermoset material (such as an Epoxy resin) is added to the mould and cured to hold the electrodes in place. A through bore is then drilled through the cured resin along the original axis of the carbon rod from which the electrodes are formed. The diameter of the through bore is arranged so that the remaining carbon connecting the two electrodes is drilled away in this step, leaving the two electrodes separated by the required distance along a flow conduit defined by the through bore.

The inventors have realised that this conventional approach of making the conductivity cell has a number of problems. Firstly, the inventors have realised that this current manufacturing approach results in approximately 95% of the carbon being thrown away (due to the machining and drilling processes). Secondly, the inventors have realised that the use of the machine tool to produce the electrodes of the desired shape and with the desired spacing, limits the number of electrodes that can be made at any one time due to the time required to mount the carbon rod into the machine tool, the time required to remove the electrode structure from the machine tool after it has being machined and due to the limited number of machine tools that are available. Finally, the inventors have realised that the traditional technique of connecting to the electrodes using circlips and soldered wires is time consuming and costly to assemble.

SUMMARY

The present invention aims to provide a conductivity cell which alleviates one or more of the above problems.

According to one aspect, the present invention provides a conductivity sensor comprising: a housing; at least two electrodes; a plurality of slots for holding each electrode in a predetermined orientation and position within the housing; and processing and excitation circuitry operable to connect to said electrodes and to determine conductivity measurements of fluid flowing through the housing. By providing slots in the housing the electrodes can be accurately positioned and held within the housing. It is therefore possible to significantly increase the utilisation of the carbon rods used to make the electrodes. In particular, the electrodes can be formed by cutting thin rectangular blocks from a carbon rod. If the thickness of each electrode cut from the rod corresponds to the thickness of the cutter, then only 50% of the carbon rod will be lost in the process. This represents a significant saving in material costs compared with the prior art type conductivity sensor described above.

Although each electrode may be held in place by a single slot, two opposing slots are preferably provided to hold the electrode in the desired position and orientated so that the electrode is transverse to a flow path along which fluid can flow through the housing.

The slots are preferably integrally formed with the housing as this allows for the accurate placement of the electrodes within the housing. In contrast if the slots are separate from the housing and are fixed to the housing by an appropriate fastener, such as a screw, then it is likely that there will be variations in the positions of the slots in the housing, which will reduce the accuracy of the final conductivity sensor. The housing is preferably a moulded component (eg of a plastics material) and the slots are integrally formed as part of an inner wall of the housing.

In one embodiment, the housing defines a moulding cavity in which the electrodes are held by said slots and the cavity is filled with a thermoset resin such as Epoxy. In this embodiment the electrodes are preferably dimensioned so that they protrude from the resin to facilitate connection to the excitation and processing circuitry. A through bore is also provided that defines a flow path between an inlet and an outlet of the sensor that passes through the housing, the resin and the electrodes. In an alternative embodiment, the electrodes may be mounted into an injection mould and then over moulded with a thermoplastic material such as PEEK (polyetherether Ketone), Noryl or other high performance thermoplastic material. In such an embodiment, the electrodes also preferably protrude from the thermoplastic material to facilitate connection to the electronics and a through bore is provided between the inlet and the outlet for the flow of fluid.

In a preferred embodiment the processing and excitation circuitry is connected to at least one of the electrodes using a connector that directly attaches to a circuit board carrying the excitation and processing circuitry and to an edge of the electrode. In this case, the connector preferably comprises one of more barbs for gripping the edge of the electrode when inserted Into the connector.

The electrodes can be of any convenient size and shape. However, they preferably have a rectangular block shape, as this is the easiest shape to make from standard elongate carbon rods.

In one embodiment, the excitation circuitry applies first and second excitation signals having first and second excitation frequencies to at least one of the electrodes and the processing circuitry uses measurements obtained for the first and second frequencies to determine a correction to be applied to the conductivity measurements that corrects for polarisation effects of the electrodes. In such an embodiment, the two frequencies can be applied simultaneously or sequentially at different times. When the signals are applied simultaneously, the processing circuit preferably includes filters to separate out the response signals at the two frequencies so that separate measurements can be made at each frequency. If the two frequency signals are applied simultaneously, then the excitation signal may comprise, for example a square wave signal in which case the two frequency signals may be the first and third harmonics of the square wave signal.

In the preferred embodiment the excitation circuitry generates individual sine wave signals at the different frequencies and comprises: a first circuit operable to generate a first square wave signal at said first frequency; a second circuit operable to generate a second square wave signal at said second frequency; a fitter operable to filter a selected one of said first and second square wave signals to generate a sine wave signal having the same frequency as the selected square wave signal; and a selector operable to select one of said first and second square wave signals to be input to said fitter.

The correction determined from the two excitation signals may be determined for each measurement of the sensor. However, in the preferred embodiment, the correction is determined Intermittently and used until an updated correction is determined. The sensor also preferably monitors the change in the correction value to detect abnormalities in the operation of the sensor, such as may be caused by deterioration of the electrodes or by a blockage in the sensor flow conduit. If such an abnormality is detected, then a warning may be output to the user (eg using a warning display or light).

The present invention also provides a method of manufacturing apparatus for use in a conductivity sensor, the method comprising: providing a housing that defines a moulding cavity; providing a plurality of slots within said moulding cavity; placing electrodes in the slots to hold them partly within the moulding cavity; filling the moulding cavity with a settable resin; setting the resin; and forming a through bore that extends through the housing, the electrodes and the resin to define a flow conduit along which fluid can flow. In this case, the apparatus for use in the sensor may be the conductivity cell that can be made and sold separately from the excitation and processing circuitry.

Slots are preferably provided on opposite sides of the housing to hold each electrode in the desired position and oriented transverse to the fluid flow through the housing. The through bore may be drilled through the set resin, the electrodes and the housing. Alternatively, a rod may be inserted through the housing and the electrodes before the resin sets and then removed after the resin has set.

The present invention also provides a method of manufacturing apparatus for use in a conductivity sensor, the method comprising: providing a mould that defines a mould cavity having a plurality of slots within said moulding cavity; placing electrodes in the slots to hold them partly within the moulding cavity; filling the moulding cavity with a thermoplastic material; setting the thermoplastic material; and forming a through bore that extends through the housing, the electrodes and the resin to define a flow conduit along which fluid can flow.

The method also preferably attaches excitation and processing circuitry to the electrodes. The attachment preferably uses connectors that directly attach to one edge of the electrodes and directly to a circuit board carrying at least part of the excitation and/or processing circuitry. The connectors preferably comprise one of more barbs for gripping the edge of the electrode when it is inserted into a groove of the connector.

The present invention also provides a conductivity sensor comprising: a housing defining a flow conduit for the passage of a fluid; first and second electrodes spaced apart along said flow conduit; excitation circuitry operable to connect to said electrodes and operable to generate excitation signals; and processing circuitry operable to connect to said electrodes and operable to determine conductivity measurements of fluid flowing through the housing; wherein said excitation circuitry is operable to apply first and second excitation signals having first and second excitation frequencies respectively, to at least one of said electrodes and wherein said processing circuitry is operable to use measurements obtained for the first and second frequencies to determine a correction to be applied to said conductivity measurements for correcting for polarisation effects of the electrodes.

The different frequency excitation signals may be applied simultaneously or one after the other. If applied simultaneously, then the processing circuitry preferably includes filters for obtaining the measurements for the first and second excitation frequencies.

The present invention also provides a conductivity sensor comprising: a housing defining a flow conduit for the passage of a fluid; first and second electrodes spaced apart along said flow conduit; excitation circuitry operable to connect to said electrodes and operable to generate excitation signals; and processing circuitry operable to connect to said electrodes and operable to determine conductivity measurements of fluid flowing through the housing; wherein at least part of said excitation and said processing circuitry are mounted on a circuit board that is connected to said electrodes by first and second edge connectors that are each directly attached to said circuit board and to an edge of a respective one of said first and second electrodes.

The edge connectors preferably include one or more barbs for gripping the edge of the electrode when inserted into the connector and are shaped to receive electrodes that have a rectangular block shape.

Those skilled in the art will appreciate that variations of detail may be provided and features of one aspect may be applied to other aspects within the scope of the invention as set out in the attached claims.

BRIEF DESCRIPTION OF THE DRAWINGS

In order to aid in the understanding of the present invention, a number of exemplary embodiments will now be described in detail with reference to the accompanying figures in which.

DETAILED DESCRIPTION

Structure of Conductivity Sensor

Figure 1:
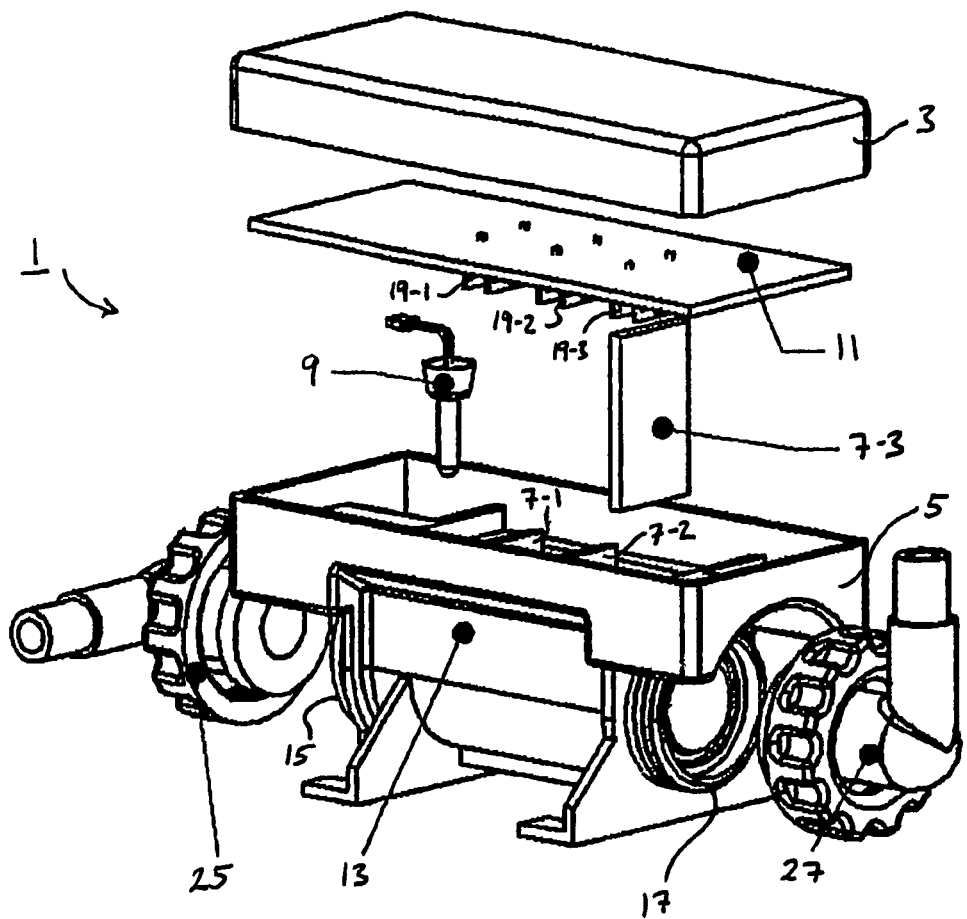
FIG. 1 is an exploded perspective view of a conductivity sensor embodying the present invention.

FIG. 1 is a three-dimensional exploded view illustrating the main components of a conductivity sensor 1 of a first embodiment of the present invention. The conductivity sensor 1 is designed as part of a dialysis machine (not shown) and provides a measurement of the main flow conductivity and temperature. The conductivity sensor 1 comprises a housing formed by an upper housing part 3 and a lower housing part 5 in which three electrodes 7-1, 7-2 and 7-3, a temperature sensor 9 and a printed circuit board (PCB) 11 carrying excitation and processing circuitry, are housed.

As will be described in more detail below, the electrodes 7 are mounted and held within the cavity of a flow channel 13 which has an inlet 15 and an outlet 17. As illustrated in FIG. 1, the printed circuit board 11 includes three connector clips 19-1, 19-2 and 19-3 which are arranged to clip onto and make an electrical connection with the minor edge of a respective one of the electrodes 7-1 to 7-3. In this embodiment the electrodes have a generally rectangular block (domino) shape which is 22 mm long, 16 mm wide and 2 mm thick.

Figure 2:
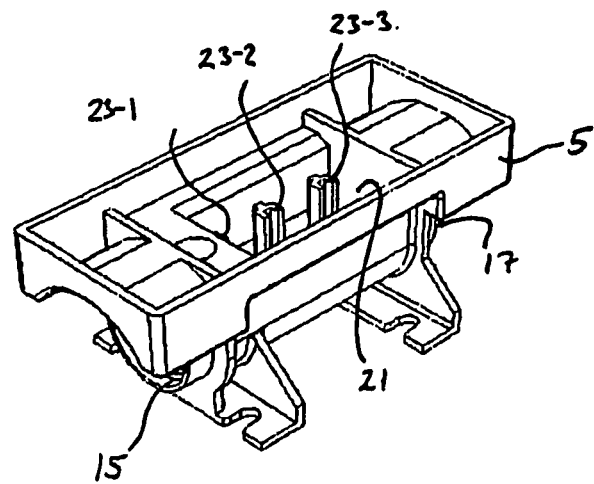
FIG. 2 is a perspective view from above of a lower half of a housing forming part of the conductivity sensor shown in FIG. 1.

The way in which the conductivity sensor 1 is made will now be described with reference to FIG. 2. Initially, the electrodes 7-1 to 7-3 are positioned and held within the elongate mould cavity 21 of the flow channel 13 by a respective pair of opposing slots, one from each pair being shown in FIG. 2 and labelled 23-1, 23-2 and 23-3. The other slot of each pair is hidden from view by the side wall of the lower housing part 5. The slots 23 are dimensioned to receive and hold the long edge of the electrodes 7 so that the electrodes 7 are held in an orientation that is transverse to the longitudinal axis of the elongate mould cavity 21. In this embodiment, the parts of the housing are formed from a plastic material, e.g Noryl® and the slots 23 are integrally moulded to the inside wall of the mould cavity 21. As the slots 23 are integrally moulded within the mould cavity 21 they can be accurately positioned and hence the electrodes can be accurately spaced apart from each other. As those skilled in the art will appreciate, accurate positioning of the electrodes is essential for defining the correct cell constant of the conductivity cell (which is defined by the area of the electrodes that will be in contact with the fluid and the separation between the electrodes).

After the electrodes 7 have been inserted within the slots 23, the mould cavity 21 is filled with a thermoset resin such as an Epoxy resin. In this embodiment, the depth of the mould cavity 21 and the length of the electrodes 7 are chosen to ensure that approximately 4 mm of each electrode 7 protrudes from the thermoset material. The thermoset resin is then degassed and cured, typically by heating. Once cured, a through bore (not shown) is drilled along the longitudinal axis of the mould cavity 21 in order to define a flow conduit between the inlet 15 and the outlet 17 that passes through the set resin and the electrodes 7.

After the thermoset resin has cured and the through bore drilled, the temperature sensor 9 is inserted to extend within the inlet 15 and the PCB 11 is connected to the ends of the electrodes 7 that protrude from the mould cavity 21 via the connector clips 19. The upper housing part 3 is then secured to the lower housing part 5 in a conventional manner. The inlet 15 and the outlet 17 of the conductivity sensor 1 are then connected to inlet and outlet pipes 25 and 27 of the dialysis machine.

Figure 3A:
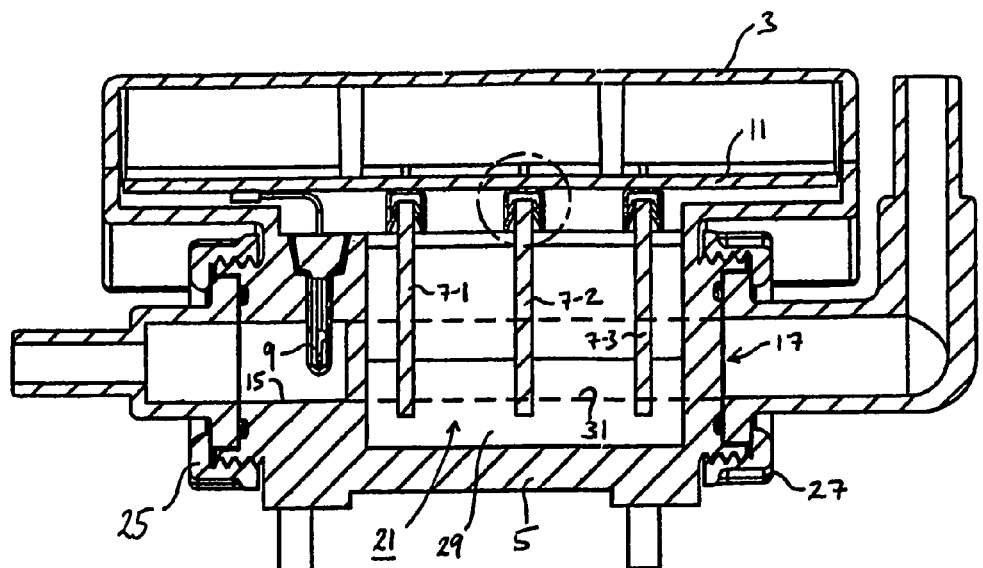
FIG. 3A is a cross-sectional view of the assembled conductivity sensor shown in FIG. 1.

FIG. 3A is a cross-sectional view along the longitudinal axis of the conductivity sensor 1 once assembled. As shown, the temperature sensor 9 extends through the side wall of the lower housing component 5 into the inlet 15 and is arranged to sense the temperature of the liquid that flows through the conductivity sensor 1. FIG. 3A also shows in more detail the moulding cavity 21 in which the thermoset resin 29 is initially poured and then cured. FIG. 3A also illustrates the through bore 31 that extends between the inlet 15 and the outlet 17 through the cured thermoset resin and the electrodes 7.

Figure 3B:
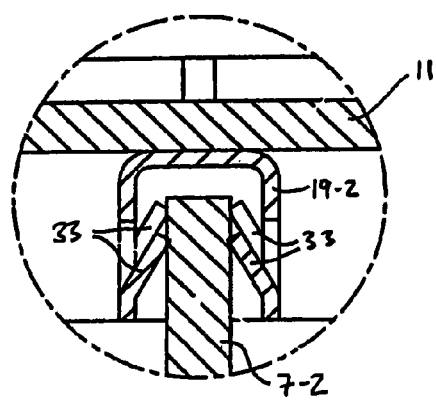
FIG. 3B is a detail view illustrating the way in which carbon electrodes are connected to a printed circuit board of the conductivity meter.
Figure 3C:
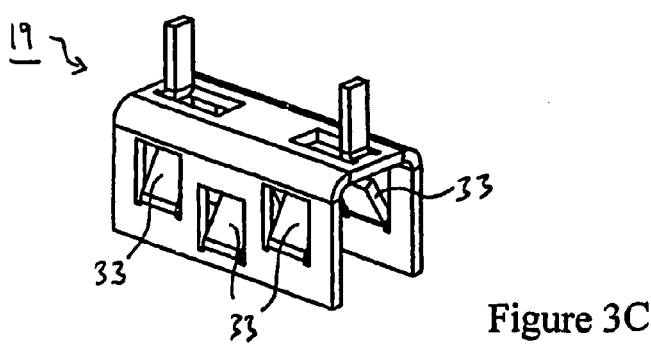
FIG. 3C is a perspective view illustrating the form of the connectors used to connect the carbon electrodes to the printed circuit board.

FIG. 3B is a detailed view of the connection clip 19-2 that connects the PCB 11 to the electrode 7-2 shown in FIG. 3A. A perspective view of one of the connector clips 19 is shown in FIG. 3C. As illustrated, the connector clips 19 include six barbed spring contacts, some of which are shown and labelled 33. These barbed spring contacts 33 are arranged to grip the end of the carbon electrode 7 when it is inserted into the connector clip 19, as illustrated in FIG. 3B.

Operation of Conductivity Sensor

Excitation circuitry mounted on the PCB 11 generates a voltage stabilised low distortion 1 Volt peak to peak sine wave signal that is applied to the centre electrode 7-2. The outer electrodes 7-1 and 7-3 are connected together and to ground via a reference resistor. The conductivity cell and the reference resistor produce a voltage divider. The voltage at the junction of the potential divider is an AC voltage proportional to the measured conductivity. Processing circuitry also mounted on the PCB 11 processes this AC voltage to determine a measurement of the conductivity of the fluid flowing through the sensor 1.

Figure 4:
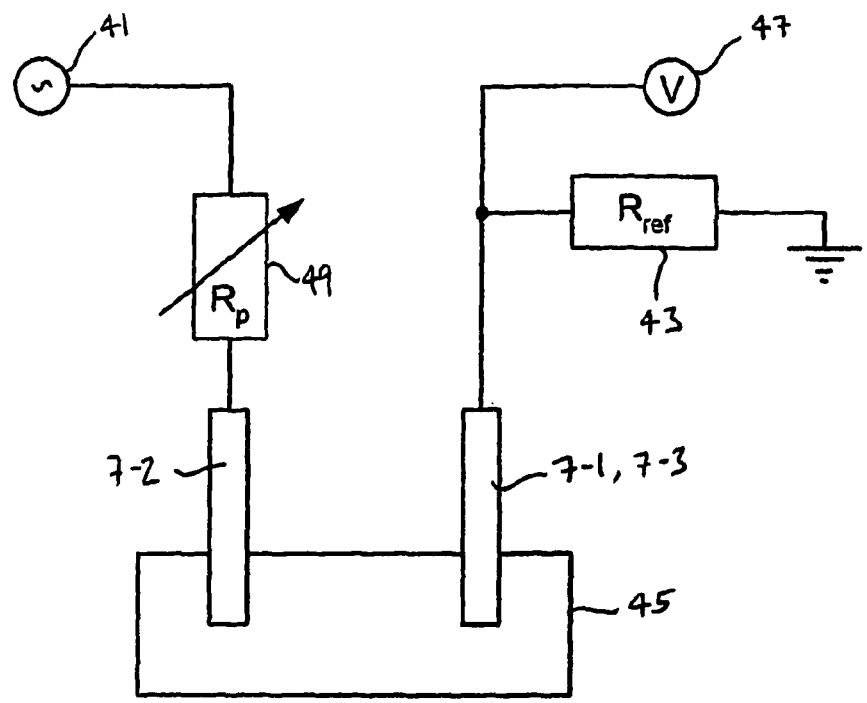
FIG. 4 is an electrical equivalent circuit of the conductivity sensor illustrated in FIG. 1.

FIG. 4 is an electrical equivalent circuit of the conductivity sensor 1. In particular, FIG. 4 shows the AC source 41 which applies an AC voltage to the central electrode 7-2. FIG. 4 also shows the two outer electrodes 7-1 and 7-3 which are connected together and to ground through the reference resistor ($R_{ref}$) 43. The fluid flowing through the through bore 31 is represented by the rectangle 45 and the processing circuitry on the PCB 11 is represented by the voltmeter 47.

As is well known, this type of conductivity sensor suffers from inaccuracies caused by polarisation effects of the electrodes 7. These polarisation effects are represented in FIG. 4 by the variable polarisation resistor ($R_p$) 49. As is well known, this polarisation resistance varies inversely with the square root of the frequency of the excitation signal. It is therefore possible (and common practice) to reduce the effect of this polarisation resistance by applying a high frequency excitation signal. However, the use of such a high frequency excitation signal requires more expensive and more complex excitation and processing circuitry and creates more difficulties due to interference and capacitive coupling between the electrodes. Another commonly used technique for trying to overcome the polarisation problem is to fix the frequency of the excitation signal and to measure the polarisation resistance (by passing a fluid of known conductivity through the meter) and to store this as calibration data which can be used to correct measurements obtained during normal use. However, the polarisation resistance for a given excitation frequency will vary slowly over time as the properties of the electrodes 7 change over time. Therefore, unless this calibration routine (which is typically carried out in the factory due to the need to use a fluid of known conductivity) is periodically re-performed, the conductivity sensor 1 will slowly become less accurate over time.

Dual Frequency Measurement

In this embodiment, the excitation and processing circuitry mounted on the printed circuit board 11 is arranged to apply two different excitation frequencies and to measure the signals obtained at those two frequencies in order to determine a measure of the polarisation resistance which can then be used to correct the conductivity measurements. This dual frequency measurement may be performed each time the conductivity sensor makes a measurement or it may be performed intermittently (during a calibration routine) with the measured polarisation data being stored for use in subsequent measurements that rely on single frequency excitation. The dual frequency excitation signals may be applied simultaneously and then separated (filtered) in the processing circuitry, but in the preferred embodiment the dual excitation frequencies are applied one after the other.

Figure 5:
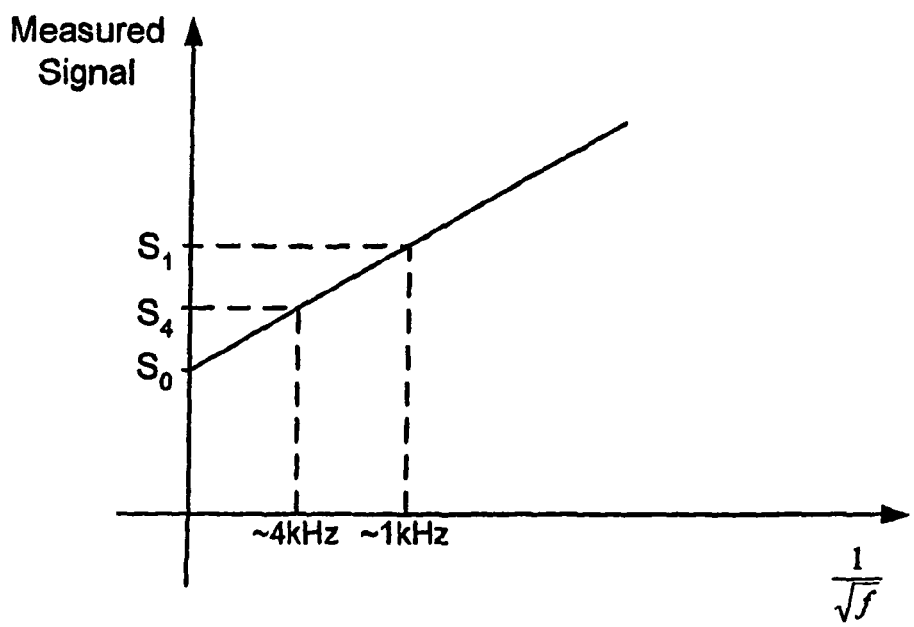
FIG. 5 is a plot illustrating the way in which the measured signals vary with applied frequency as a result of polarisation effects associated with the electrodes.

FIG. 5 is a plot illustrating the way in which the measured signal varies with the reciprocal of the square root of the applied frequency (f). As illustrated, as the excitation frequency decreases, the measured signal increases and when the excitation frequency increases, the measured signal reduces to a value $S_0$ that corresponds to the desired signal that is proportional to the conductivity of the fluid flowing through the sensor 1. In this embodiment, in order to make the calculations easier, excitation frequencies of 4 kHz and 1 kHz are used. By using these frequencies, the difference between the measured signal ($S_4$) obtained when applying the 4 kHz excitation signal and the measured signal ($S_1$) obtained when applying the 1 kHz excitation signal is approximately equal to the difference between the measured signal ($S_4$) obtained when the 4 kHz excitation signal is applied and the corrected conductivity measure $S_0$. In other words $S_1-S_4=S_4-S_0$ and therefore $S_0=2S_4-S_1$. However, as discussed above, the conductivity sensor 1 may not use two excitation frequencies each time that it takes a conductivity measurement. To cope with this, the processing circuitry determines the value of $S_1-S_4$ and stores this as a calibration value, which it subtracts from a subsequent measurement obtained when a single excitation signal (at 4 kHz) is applied to the electrode 7-2. The result is a corrected conductivity measure ($S_0$).

As those skilled in the art will appreciate, it is not essential to employ these two specific frequencies during the dual frequency measurement. Other frequency values can be used which lead to similar relationships between the measured signal values and the corrected conductivity measure ($S_0$). For example, excitation frequencies of 4 kHz and 16 kHz will provide similar results. Further, it is not essential to use excitation frequencies that are related in the above manner. Any two excitation frequencies may be used, although this will require more complicated processing of the measured signals by the processing circuitry. In particular, in this case the processing circuitry will have to store data defining the variation of the measured signal with applied frequency so that the processing electronics can use the two measured signals and relate them to the two unknowns—the polarisation resistance ($R_p$) and the conductivity of the fluid flowing through the sensor 1.

Excitation and Processing Circuitry

Figure 6:
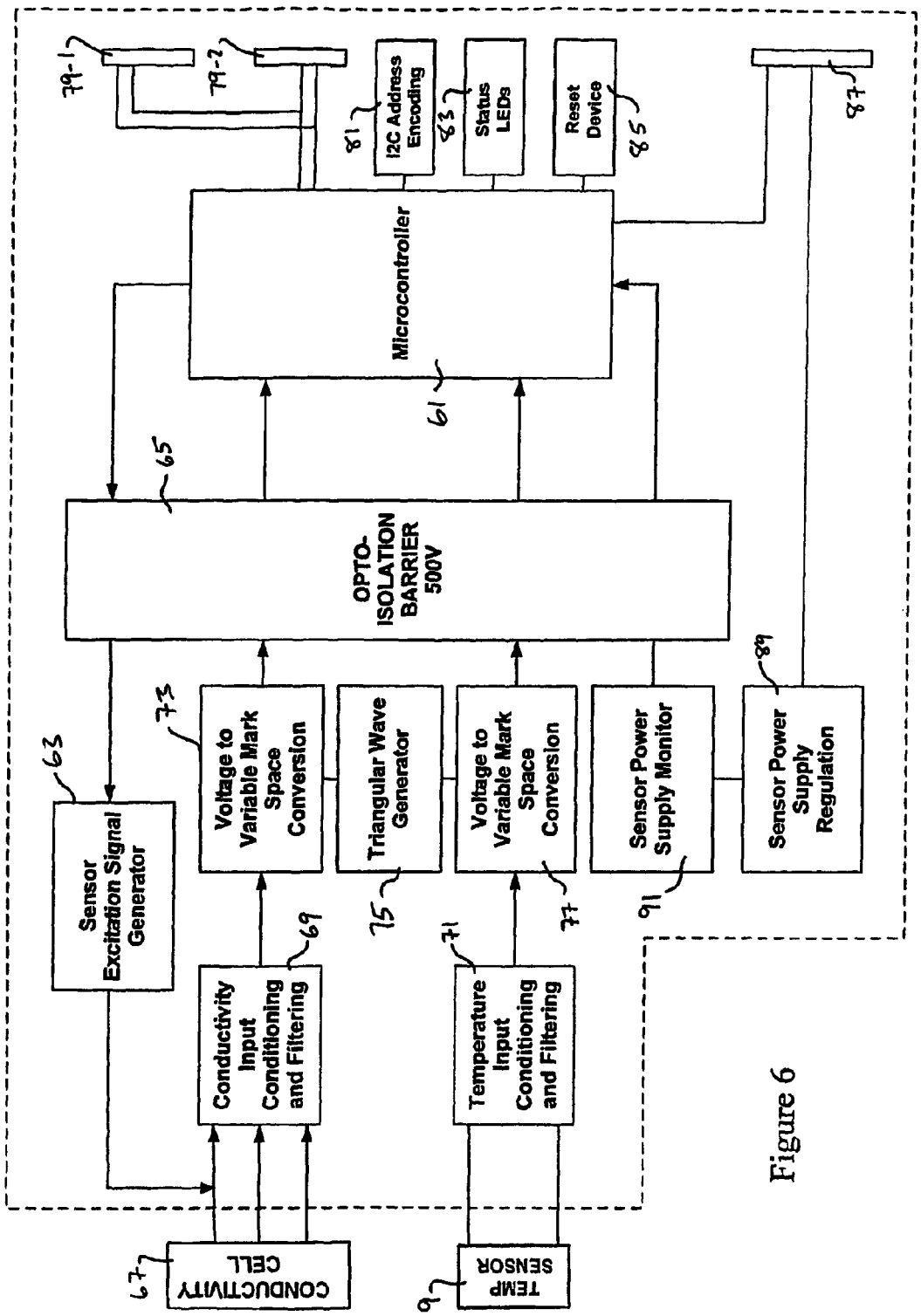
FIG. 6 is a block diagram illustrating the excitation and processing circuitry forming part of the conductivity sensor shown in FIG. 1.
Figure 7:
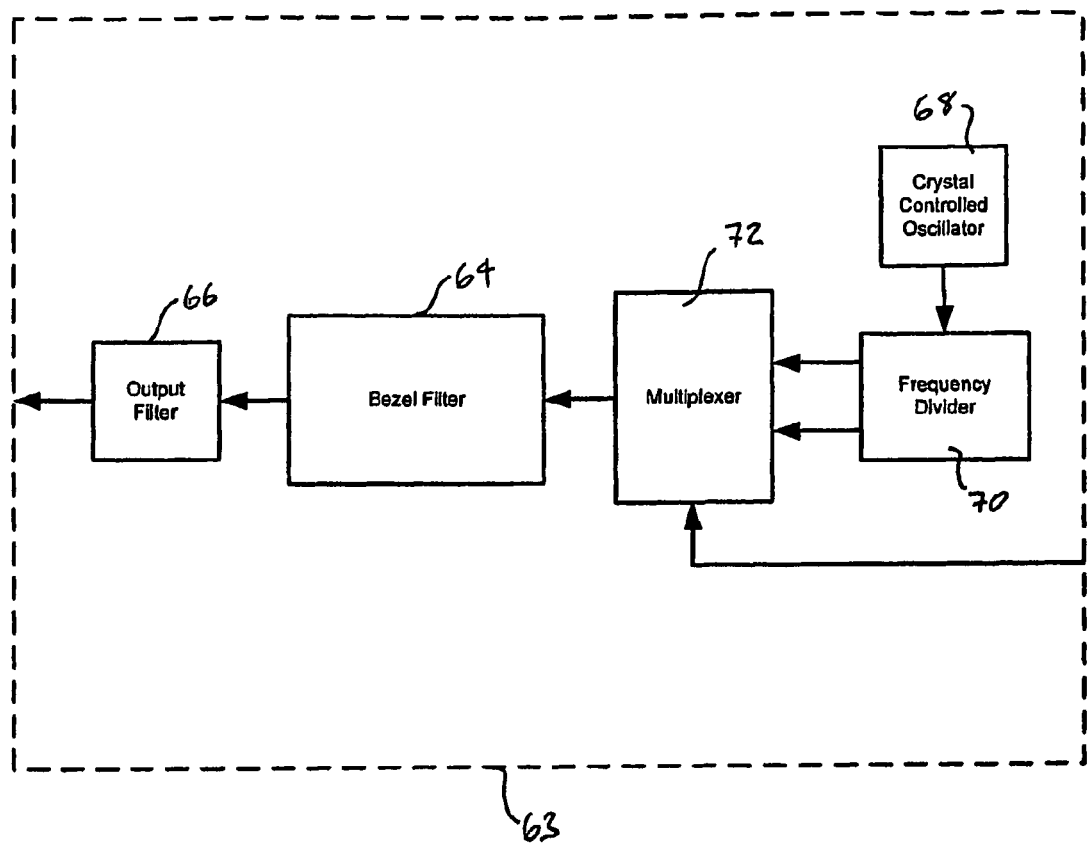
FIG. 7 is a block diagram illustrating the main components of excitation circuitry that forms part of the circuitry shown in FIG. 6.
Figure 8:
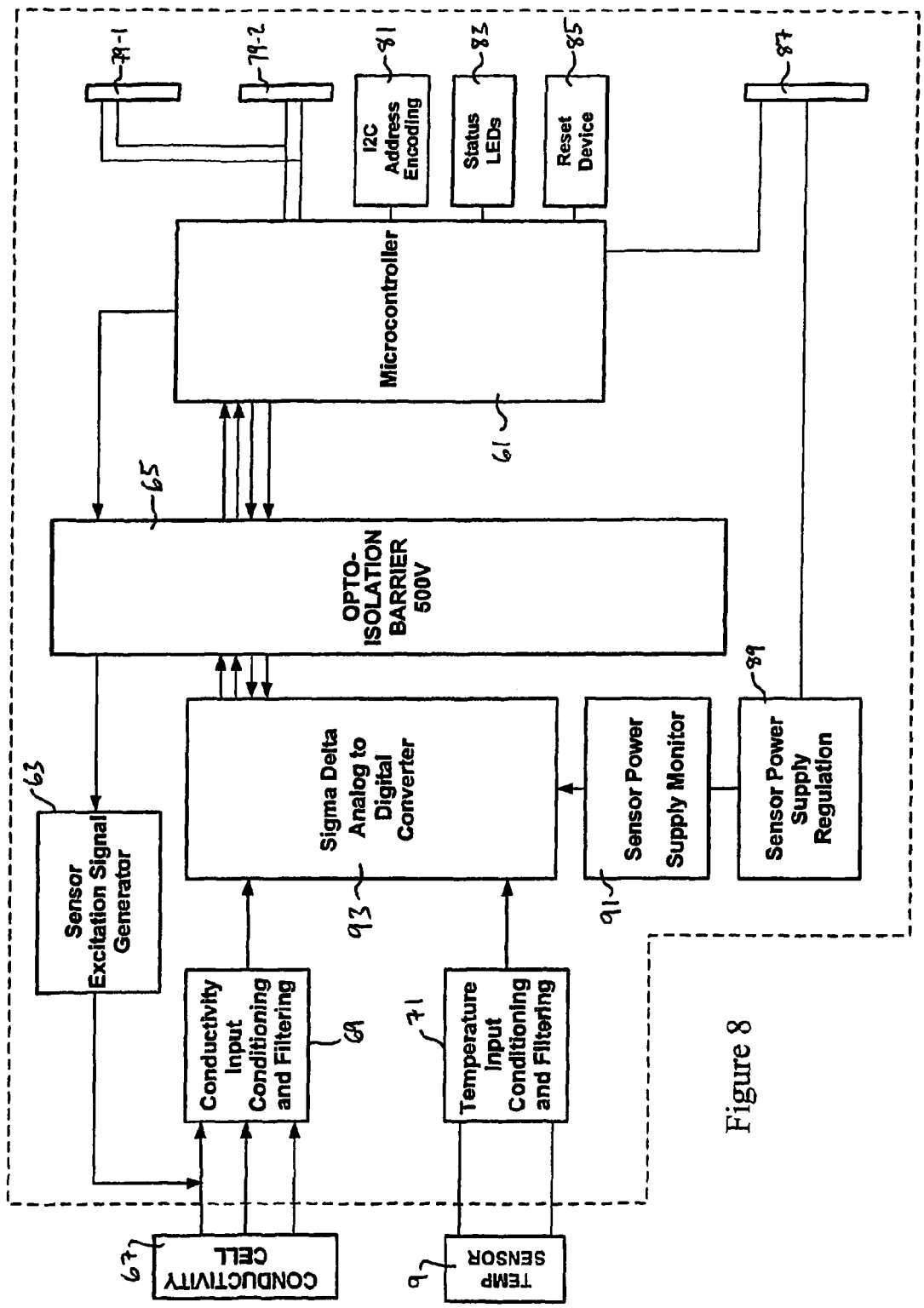
FIG. 8 is a block diagram illustrating an alternative arrangement of the excitation and processing circuitry.

FIG. 6 is a block diagram illustrating the main components of the excitation and processing circuitry mounted on the printed circuit board 11. As shown, the circuitry includes a microcontroller 61 which generates appropriate control signals for controlling the generation of the excitation signal by the sensor excitation signal generator 63. As shown, in FIG. 6, an opto-isolation barrier 65 is provided between the microcontroller 61 and the excitation signal generator 63. In this embodiment, the excitation signal generator 63 generates a voltage stabilised low-distortion sine wave at the frequency selected by the microcontroller 61. In this embodiment, as illustrated in FIG. 7, the sensor excitation signal generator 63 generates this sine wave using an $8^{th}$ order bezel filter 64 together with output filtering 66 to smooth the waveform. To function, the bezel filter 64 requires a square wave at the required output frequency together with a clock running at a frequency of 128 times the required frequency. A crystal controlled oscillator 68 and a frequency divider 70 are used to create these signals. In this embodiment, to allow for the use of frequency switching to eliminate polarisation effects, two sets of clocks and output frequencies are provided by the frequency divider 70 and a dual digital multiplexer 72 is used to select the required set of frequencies as the input to the bezel filter 64. The microcontroller 61 controls the multiplexer 72 so that the appropriate excitation signal is applied to electrode 7-2 of the conductivity cell 67.

As shown, in FIG. 6, the signals from the electrodes 7 are input to a conductivity input conditioning and filtering circuit 69 which filters the incoming signals to reduce the effects of noise. The input conditioning and filtering circuitry then rectifies and smoothes the signal to produce a DC signal that varies with the conductivity of the fluid flowing through the conductivity cell 67. Finally, the input conditioning filtering circuitry 67 amplifies and scales this DC signal to improve the signal to noise ratio prior to analogue to digital conversion.

FIG. 6 also shows the temperature sensor 9. In this embodiment, the temperature of the fluid is also measured by creating a potential divider with a reference resistor (not shown) and a sensor. The reference resistor is chosen to minimise the current passing through the temperature sensor 9 to a level which eliminates errors due to self heating. The temperature sensor is driven by applying a fixed DC voltage and the resulting measured DC signal is filtered and scaled prior to analogue to digital conversion by the temperature input conditioning and filtering circuit 71.

In this embodiment, the amplified and scaled DC signal output by the conditioning and filtering circuitry 69 is input to a voltage to variable mark space conversion circuit 73 where it is compared with the current value of a triangular wave generated by a triangular wave generator 75. The resulting output will therefore be a fixed frequency signal (corresponding to the frequency of the triangular wave generator) having a mark space ratio that is proportional to the DC signal output from the conditioning and filtering circuit 69. This mark space signal is then fed via the optical-isolation barrier 65 to a timer compare input of the microcontroller 61 which performs a high resolution measurement of the mark and space times from which it calculates the mark space ratio, which corresponds to the value of $S_4$ or $S_1$ discussed above (depending on the excitation frequency used).

An equivalent analogue to digital conversation is performed on the filtered and scaled DC signal output by the temperature input conditioning and filtering circuit 71 using the voltage to variable mark space conversion circuit 77.

As shown in FIG. 6, the processing circuitry mounted on the printed circuit board 11 also includes an i2c interface 79-1 and 79-2 from which the corrected conductivity measurements can be output to, for example, another computer device. An i2c address encoding circuit 81 is also provided for providing address information to the microcontroller 61 for controlling the communications over the i2c output bus 79. Status LEDs 83 are also provided and controlled by the microcontroller 61. In particular, the microcontroller 61 controls the status LEDs 83 to indicate to a user whether or not the conductivity sensor 1 is operating correctly. The microcontroller 61 can identify if there is a fault by, for example, monitoring the way in which the measured polarisation resistance changes over time. In particular, if the polarisation resistance suddenly changes by more than a predetermined amount from previous values, then this is an indication that there is a malfunction with the sensor 1. Accordingly, the microcontroller 61 can output an appropriate warning to the user by activating an appropriate status LED 83.

As shown in FIG. 6, a reset device 85 is also provided and coupled to the microcontroller 61 for resetting the conductivity sensor 1 to its original factory settings. Finally, the circuitry includes a power supply connector 87 for receiving power from an external supply which is passed to the microcontroller 61 and to a sensor power supply regulation circuit 89 which controls the power level of the signals applied to the electrodes 7 and to the temperature sensor 9. A sensor power supply monitor 91 is also provided for monitoring the sensor supply generated by the regulation circuit 89 and this monitored power information is also supplied to the microcontroller 61 for use in monitoring the status of the conductivity sensor 1.

Modifications and Alternative Embodiments

In the above embodiments, the signals obtained from the electrodes 7 and the temperature sensor 9 were digitised using a particular type of analogue to digital converter. FIG. 7 is a block diagram illustrating the excitation and processing circuitry used in an alternative embodiment where a different type of analogue to digital conversion circuit is provided. In particular, in this alternative embodiment, a Sigma Delta analogue to digital converter 93 is provided that has separate inputs for the conductivity and temperature signals. The Sigma Delta analogue to digital converter 93 has the advantage of providing good 50/60 Hz noise rejection without the need for additional filtering stages and includes a built-in gain stage that eliminates the need for some of the gain and scaling circuitry in the conditioning and filtering circuits 69 and 71.

As discussed above, two excitation signals of different frequencies are applied to the electrodes 7 of the conductivity sensor 1. In the specific embodiment that is described, the two signals were applied sequentially. Provided the conductivity of the fluid being measured does not change significantly during the time internal between the application of the two excitation signals, the above calculations allow for the determination of the polarisation resistance ($R_p$), or at least a measure ($S_4$-$S_1$) that is proportional to this resistance. One of the advantages of the technique described above is that the calculations to determine the polarisation resistance do not require knowledge of the conductivity of the fluid passing through the conductivity sensor 1. Therefore, the measurements can be performed at any time and do not require any special off-line processing.

As mentioned above, instead of applying the two excitation signals at different times, the two excitation signals may be applied to the electrode 7-2 at the same time. This may be achieved, for example, by applying a square wave signal that includes a fundamental frequency component and higher order harmonics. By filtering the signals obtained from the electrodes 7 at the fundamental frequency and at the third harmonic, two measurements at two different frequencies can be obtained. The filtering can be performed by analogue or digital filters or by a frequency analysis of the signals obtained from the electrodes. Once filtered, the measurements can then be processed in the manner outlined above to determine the effective polarisation resistance and hence correct the conductivity measurement.

In the above embodiment, the through bore 31 that defines the flow conduit through the conductivity sensor is formed by drilling longitudinally along the housing between the inlet and the outlet. In an alternative embodiment, the housing and the electrodes may be pre-drilled and an elongate rod may be inserted between the inlet and the outlet through the housing and the electrodes. In such an embodiment the rod would be inserted prior to the setting of the thermoset resin. Once the resin has set, the rod is extracted to leave a through bore that passes between the inlet and the outlet of housing.

In the above embodiments, the conductivity sensor included three electrodes, two of which where connected together and connected to ground via a reference resistor. As those skilled in the art will appreciate, it is not essential to use three electrodes. For example, a two electrode sensor may be provided in which one of the electrodes is connected to the excitation circuitry and the other electrode is connected to the processing circuitry. More electrodes may also be used if desired. Additionally, it is possible to reverse the electrodes that are connected to the excitation and processing circuitry. For example, instead of connecting the excitation circuitry to the sensor electrode 7-2 and the outer electrodes 7-1 and 7-3 to the processing circuitry, the excitation circuitry may be connected to the electrodes 7-1 and 7-3 and the processing circuitry may be connected to the sensor electrode 7-2.

Similarly, although in practice it is likely that the excitation circuitry will always be connected to the same electrode for the two frequency measurements, it is possible to apply one of the excitation frequencies to one electrode and obtain measurements from one or more of the other electrodes and to apply the second excitation frequency to the electrode previously connected to the processing circuitry and to process the signal obtained from the electrode previously connected to the excitation circuitry.

In the above embodiments, three pairs of slots are provided in the housing for receiving and holding the three electrodes. In an alternative embodiment, an array of slots (eg ten slots) may be provided along the length of the housing to allow flexibility in the positioning of the electrodes within the housing, to thereby control the resulting cell constant of the conductivity cell. Such a design has the advantage that the same housing can be used for conductivity cells having different cell constants.

In the first embodiment described above, the slots were integrally moulded with the inner wall of the housing. In an alternative embodiment, the slots may be fixed within the housing glue or an appropriate fastener, such as a screw.

In the above embodiment, the excitation and processing circuitry was mounted on a printed circuit board which was then connected directly to the electrodes via edge connectors that were directly connected to the circuit board and the edges of the electrodes. As those skilled in the art will appreciate, some of the excitation and processing circuitry may be mounted on a separate circuit board which is connected to the circuit board carrying the edge connectors. However, such an arrangement over complicates the design of the sensor and is not preferred.

Although the above embodiments have used excitation and processing circuitry formed from various hardware circuits, the functionality of the excitation and processing circuitry may be carried out by a programmable computer device and the instructions for causing the computer to carry out this functionality may be provided as a signal or as instructions stored on a computer readable medium.

Each feature disclosed in this specification (which term includes the claims) and/or shown in the drawings may be incorporated in the invention independently of other disclosed and/or illustrated features.

In the above embodiment, a thermoset resin was used to fill the cavity of a housing to surround the electrodes in the housing. In an alternative embodiment, a mould may be provided that defines a mould cavity having a plurality of slots. The electrodes may then be placed in the slots and the mould cavity filled with a thermoplastic material. Once set, the thermoplastic and embedded electrodes can be removed from the mould and drilled as before to define a flow conduit through the plastic and electrodes along which fluid can flow.

What is claimed is:

1. A method of manufacturing an apparatus for a conductivity sensor, the method comprising:
   providing a mold or housing that defines a molding cavity
   providing a plurality of slots within said molding cavity;
   placing electrodes formed of a first conductive material in the slots to hold them partly within the molding cavity;
   providing a settable second material within the molding cavity before the second material has set, wherein the second material is different from the first material;
   setting the settable second material within the mold cavity; and
   after the electrodes and settable material have been placed within the mold or housing, forming a through bore that extends through said electrodes and said settable second material to define a flow conduit that passes through the mold or housing and along which fluid can flow; and
   wherein the slots are positioned within said molding cavity so that the electrodes are spaced apart along said flow conduit.

2. A method according to claim 1, wherein providing slots provides first and second slots for holding each electrode.

3. A method according to claim 2, wherein providing slots provides first and second slots for each electrode that are positioned on opposite sides of the mold or housing for holding the electrodes spaced apart along, and in an orientation that is transverse to a flow path along which fluid can flow.

4. A method according to claim 1, wherein providing the housing provides a molded housing and wherein providing said slots provides slots that are integrally molded within the housing.

5. A method according to claim 1, wherein providing said slots provides a multiplicity of slots at different positions along the length of the molding cavity and wherein placing the electrodes includes selecting a subset of said slots into which the electrodes will be placed, depending upon a desired cell constant for the conductivity sensor.

6. A method according to claim 1, further comprising attaching excitation and processing circuitry to said electrodes using connectors that attach to an edge of the electrode that is free from said settable second material.

7. A method according to claim 6, wherein attaching said processing and excitation circuitry to said electrodes uses connectors that comprise one or more barbs for gripping the edge of the electrode when inserted into a groove of the connector.

8. A method according to claim 6, wherein attaching said processing and excitation circuitry to said electrodes uses connectors that directly attach to a printed circuit board carrying said excitation and processing circuitry.

9. A method according to claim 1, wherein placing electrodes is performed after providing said settable second material, but before setting said second material.

10. An apparatus for a conductivity sensor, the apparatus comprising:
    a housing that defines a molding cavity;
    at least two electrodes formed of a first conductive material;
    a plurality of slots for holding the electrodes in predetermined positions at least partly within the molding cavity of the housing;
    a set second material within the molding cavity, wherein the second material is different from the first material; and
    a through bore that extends through the set second material and the at least two electrodes to define a flow conduit that passes through the housing and along which fluid can flow; and
    wherein the slots are positioned within said molding cavity so that the electrodes are spaced apart along said flow conduit.

11. An apparatus according to claim 10, wherein first and second slots are provided for holding each electrode which are positioned on opposite sides of the housing for holding the electrodes in an orientation that is transverse to said flow conduit.

12. An apparatus according to claim 10, wherein said housing is molded and wherein said slots are integrally molded within the housing.

13. An apparatus according to claim 10, comprising a multiplicity of slots at different positions along the length of the molding cavity and wherein the electrodes are positioned with a selected subset of said slots, selected in dependence upon a desired cell constant for the conductivity sensor.

14. An apparatus according to claim 10, further comprising processing and excitation circuitry for determining conductivity measurements, and connectors for connecting the processing and excitation circuitry to said electrodes, and wherein at least one of said connectors is directly attached to a circuit board carrying said circuitry and to an edge of the electrode.

15. An apparatus according to claim 14, wherein said at least one connector comprises one or more barbs for gripping the edge of the electrode when inserted into a groove of the connector.

16. An apparatus according to claim 10, comprising excitation circuitry operable to apply first and second excitation signals having first and second excitation frequencies respectively, to at least one of said electrodes and processing circuitry operable to use measurements obtained for the first and second frequencies to determine a correction to be applied to conductivity measurements that corrects for polarisation effects of the electrodes.

17. An apparatus according to claim 16, wherein said excitation circuitry comprises:
    i) a circuit operable to generate a first square wave signal at said first frequency and a second square wave signal at said second frequency;
    ii) a filter operable to filter a selected one of said first and second square wave signals to generate a sine wave signal having the same frequency as the selected square wave signal; and
    iii) a selector operable to select one of said first and second square wave signals to be input to said filter.

18. An apparatus according to claim 16, wherein said excitation circuitry is operable to apply said first and second excitation signals and said processing circuitry is operable to determine said correction during a calibration routine that is performed from time to time and wherein said processing circuitry is operable to store the determined correction for use in correcting subsequent measurements until a further calibration routine is performed and an updated correction is determined.

19. A sensor according to claim 18, wherein said processing circuitry is operable to determine status information indicative of the operating status of the sensor by comparing the updated correction with one or more previous corrections.

20. An apparatus according to claim 16, wherein the frequencies of said first and second excitation signals are chosen so that said processing circuit can determine said correction by subtracting the measurements obtained for the first and second excitation frequencies.

* * * * *